US010716566B2

(12) United States Patent
Breiner

(10) Patent No.: US 10,716,566 B2
(45) Date of Patent: Jul. 21, 2020

(54) APPARATUS AND METHOD FOR USE OF A MULTI-DEGREE-OF-FREEDOM SURGICAL CLIP

(71) Applicant: Edward Via Virginia College of Osteopathic Medicine, Blacksburg, VA (US)

(72) Inventor: Michael Breiner, Roanoke, VA (US)

(73) Assignee: EDWARD VIA VIRGINIA COLLEGE OF OSTEOPATHIC MEDICINE, Blacksburg, VA (US)

( * ) Notice: Subject to any disclaimer, the term of this patent is extended or adjusted under 35 U.S.C. 154(b) by 145 days.

(21) Appl. No.: 16/123,145

(22) Filed: Sep. 6, 2018

(65) Prior Publication Data

US 2019/0105045 A1    Apr. 11, 2019

Related U.S. Application Data

(60) Provisional application No. 62/570,236, filed on Oct. 10, 2017.

(51) Int. Cl.
| | | |
|---|---|---|
| A61B 17/08 | (2006.01) | |
| A61B 17/122 | (2006.01) | |
| A61B 17/24 | (2006.01) | |
| A61B 17/128 | (2006.01) | |

(52) U.S. Cl.
CPC ........ *A61B 17/083* (2013.01); *A61B 17/1227* (2013.01); *A61B 17/24* (2013.01); *A61B 17/1285* (2013.01); *A61B 2017/081* (2013.01); *A61B 2017/1225* (2013.01)

(58) Field of Classification Search
CPC ... A61B 17/0487; A61B 17/08; A61B 17/083; A61B 17/805; A61B 17/12; A61B 17/1327; A61B 2017/081; A61B 2017/086; A61B 2017/088; A61B 2017/12004; A61B 2017/1225; A61B 2017/1227; A61M 39/289; A61M 39/284; Y10T 24/44222; Y10T 24/44342; Y10T 24/44359; Y10T 24/44376; Y10T 24/44385; Y10T 24/44393; Y10T 24/44402; Y10T 24/4441; Y10T 24/44419; Y10T 24/44427; Y10T 24/44436; Y10T 24/44444; Y10T 24/44462; Y10T 24/4447; Y10T 24/44479
USPC .................................................. 606/157, 158
See application file for complete search history.

(56) References Cited

U.S. PATENT DOCUMENTS

| | | |
|---|---|---|
| 1,437,995 A | 12/1922 | Richter |
| 4,467,803 A | 8/1984 | Ngo |
| 4,681,109 A | 7/1987 | Arroyo |

(Continued)

*Primary Examiner* — Martin T Ton
(74) *Attorney, Agent, or Firm* — Tarolli, Sundheim, Covell & Tummino LLP

(57) ABSTRACT

A dual-directional, or multi-degree-of-freedom, surgical clip is provided. The clip includes a top clamp. A bottom clamp is hingedly connected to the top clamp at a hinged joint for mutually pivotal transverse motion about the hinged joint. The top and bottom clamps each include a hinged attachment at an extreme end thereof. A first portion of each of the top and bottom clamps is in hinged connection with a corresponding second portion of the respective top and bottom clamps for mutually pivotal lateral movement. A method of using the clip to concurrently grasp and move patient tissue is also provided.

18 Claims, 6 Drawing Sheets

(56) References Cited

U.S. PATENT DOCUMENTS 5,482,263 A * 1/1996 Kutzleb .................. B25B 5/142
269/6
2007/0112365 A1 5/2007 Hilal et al.

* cited by examiner

APPARATUS AND METHOD FOR USE OF A MULTI-DEGREE-OF-FREEDOM SURGICAL CLIP

RELATED APPLICATION

This application claims priority from U.S. Provisional Application No. 62/570,236 filed 10 Oct. 2017, and is related to U.S. Design Patent application No. 29/662,512, filed concurrently herewith and titled "MULTI-DEGREE-OF-FREEDOM SURGICAL CLIP". the subject matter of both of which is incorporated herein by reference in its entirety for all purposes.

TECHNICAL FIELD

This disclosure relates to an apparatus and method for use of a multi-degree-of-freedom surgical clip and, more particularly, to a method and apparatus for concurrently grasping/clamping and moving patient tissue.

BACKGROUND

Though epinephrine is often used to help control bleeding during lesion excision, the repair of lip/facial lacerations, and other accessible surface procedures, it may be difficult to employ in the lip/mouth use environment due to the very quick absorption in that vessel-rich environment (which could result in tachycardia) and the potential for undesirable heart issues, particularly in the elderly patient population, where there is also a predilection to oral lesions and cancers. In addition, the use of epinephrine in the lip causes vascular constriction and blanching of the "red" portion of the lip, thus replicating the color of the surrounding skin. When the "redder" lip color is not available as a guide, the alignment of the wound edges can become quite complicated and imprecise.

Furthermore, lip lacerations bleed profusely, possibly resulting in significant blood loss. In addition, due to the red lip mucosa and facial skin interface in the lip area, it may be desirable to carefully approximate and control motion of the lip/mouth tissues to avoid a "mismatch" or other unwanted visible artifact of the surgical process.

SUMMARY

In an aspect, a dual-directional surgical clip is disclosed. The clip includes a top clamp. A bottom clamp is hingedly connected to the top clamp at a hinged joint for mutually pivotal transverse motion about the hinged joint. The top and bottom clamps each include a hinged attachment at an extreme end thereof. A first portion of each of the top and bottom clamps is in hinged connection with a corresponding second portion of the respective top and bottom clamps for mutually pivotal lateral movement.

In an aspect, a multi-degree-of-freedom surgical clip is disclosed. The clip includes a pair of top legs. Each top leg includes oppositely disposed proximal and distal top leg ends. The distal top leg ends are hingedly attached together for mutual pivotal movement along a lateral direction. A pair of bottom legs is provided. Each bottom leg includes oppositely disposed proximal and distal bottom leg ends. The distal bottom leg ends are hingedly attached together for mutual pivotal movement along the lateral direction. A hinged joint is located proximally from the distal top and bottom leg ends and connects the pairs of top and bottom legs together for mutual pivotal movement along a transverse direction In an aspect, a method of concurrently grasping and moving patient tissue is disclosed. A dual-directional surgical clip including a top clamp is provided. A bottom clamp is hingedly connected to the top clamp at a hinged joint for mutually pivotal transverse motion about the hinged joint. The top and bottom clamps each include a hinged attachment at an extreme end thereof. A first portion of the top and bottom clamps is in hinged connection with a corresponding second portion of the top and bottom clamps for mutually pivotal lateral movement. Transversely directed force is exerted on at least one of the top and bottom clamps to relatively pivot the top and bottom clamps about the hinged joint in an opening direction, thus causing distal portions of the top and bottom clamps to separate. A patient tissue is inserted between the separated distal portions of the top and bottom clamps. With the patient tissue inserted therebetween, transversely directed force is exerted on at least one of the top and bottom clamps to relatively pivot the top and bottom clamps about the hinged joint in a closing direction, thus causing distal portions of the top and bottom clamps to approximate and thereby grasp the patient tissue. The patient tissue is maintained grasped between the top and bottom clamps. With the patient tissue maintained between the top and bottom clamps, laterally directed force is exerted concurrently on both the top and bottom clamps to pivot the first portions of the top and bottom clamps into a predetermined lateral position with respect to the second portions of the top and bottom clamps.

BRIEF DESCRIPTION OF THE DRAWINGS

For a better understanding, reference may be made to the accompanying drawings, in which.

DESCRIPTION OF ASPECTS OF THE DISCLOSURE

Figure 1:
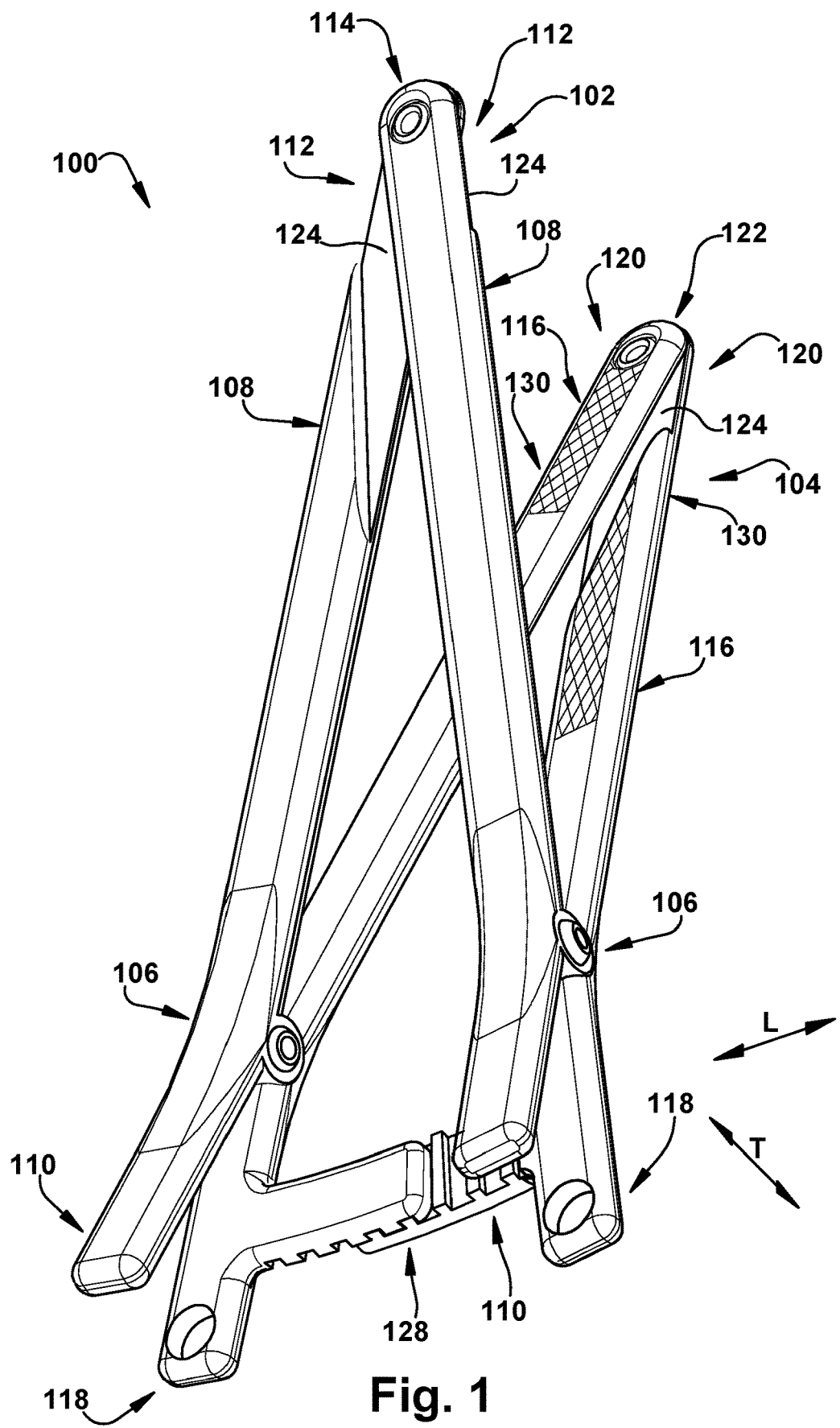
FIG. 1 is a side perspective view of a surgical clip according to an aspect of the present invention.

Unless defined otherwise, all technical and scientific terms used herein have the same meaning as is commonly understood by one of skill in the art to which the present disclosure pertains.

As used herein, the term "patient" can be used interchangeably with the term "subject" and refer to any warm-blooded organism including, but not limited to, human beings, pigs, rats, mice, dogs, goats, sheep, horses, monkeys, apes, rabbits, cattle, farm animals, livestock, etc.

As used herein, the singular forms "a," "an" and "the" can include the plural forms as well, unless the context clearly indicates otherwise. It will be further understood that the terms "comprises" and/or "comprising," as used herein, can specify the presence of stated features, steps, operations, elements, and/or components, but do not preclude the presence or addition of one or more other features, steps, operations, elements, components, and/or groups thereof.

As used herein, the term "and/or" can include any and all combinations of one or more of the associated listed items.

It will be understood that when an element is referred to as being "on," "attached" to, "connected" to, "coupled" with, "contacting," etc., another element, it can be directly on, attached to, connected to, coupled with or contacting the other element or intervening elements may also be present. In contrast, when an element is referred to as being, for example, "directly on," "directly attached" to, "directly connected" to, "directly coupled" with or "directly contacting" another element, there are no intervening elements present. It will also be appreciated by those of skill in the art that references to a structure or feature that is disposed "directly adjacent" another feature may have portions that overlap or underlie the adjacent feature, whereas a structure or feature that is disposed "adjacent" another feature might not have portions that overlap or underlie the adjacent feature.

Spatially relative terms, such as "under," "below," "lower," "over," "upper" and the like, may be used herein for ease of description to describe one element or feature's relationship to another element(s) or feature(s) as illustrated in the figures. It will be understood that the spatially relative terms can encompass different orientations of a device in use or operation, in addition to the orientation depicted in the figures. For example, if a device in the figures is inverted, elements described as "under" or "beneath" other elements or features would then be oriented "over" the other elements or features.

It will be understood that, although the terms "first," "second," etc. may be used herein to describe various elements, these elements should not be limited by these terms. These terms are only used to distinguish one element from another. Thus, a "first" element discussed below could also be termed a "second" element without departing from the teachings of the present disclosure. The sequence of operations (or steps) is not limited to the order presented in the claims or figures unless specifically indicated otherwise.

The invention comprises, consists of, or consists essentially of the following features, in any combination.

FIG. 1 depicts a dual-directional surgical clip 100, also known as a multi-degree-of-freedom surgical clip 100. The clip 100 includes a top clamp 102 and a bottom clamp 104. The top clamp 102 includes a pair of top legs 108. Each top leg 108 includes oppositely disposed proximal and distal top leg ends 110 and 112, respectively. The distal top leg ends 112 are hingedly attached together (i.e., at hinged attachment 114) for mutual pivotal movement along a lateral direction. The lateral direction is substantially parallel to arrow "L" in the Figures.

Similarly, the bottom clamp 104 includes a pair of bottom legs 116. Each bottom leg 116 includes oppositely disposed proximal and distal bottom leg ends 118 and 120. The distal bottom leg ends 120 are hingedly attached together (i.e., at hinged attachment 122) for mutual pivotal movement along the lateral direction.

The bottom clamp 104 is hingedly connected to the top clamp 102 at a hinged joint 106 for mutually pivotal transverse motion about the hinged joint 106. That is, the hinged joint 106 is located proximally from the distal top and bottom leg ends 112 and 120 and connects the pairs of top and bottom legs 108 and 116 (which themselves collectively comprise the top and bottom clamps 102 and 104) together for mutual pivotal movement along the transverse direction. The transverse direction is substantially parallel to arrow "T" in the Figures and is substantially perpendicular to the lateral direction.

As shown in the Figures, the distal top leg ends 112 are directly hingedly attached to one another, as are the distal bottom leg ends 118. Stated differently, the top and bottom clamps 102 and 104 each include a hinged attachment 114 and 122, respectively, at an extreme end thereof. A first portion (e.g., a chosen one of top or bottom legs 108 and 116) of each of the top and bottom clamps 102 and 104 is in hinged connection with a corresponding second portion (e.g., another of the same type of the top or bottom legs 108 and 116) of the respective top and bottom clamps 102 and 104 for mutually pivotal lateral movement, as will be described below. The first and second portions may be directly hingedly attached to one another at the hinged attachment 114 or 122, or the hinged attachment may be indirect, such as via an intervening bearing or other rotating member. (As referenced herein, the term "first portion" refers to one leg of a clamp, and the term "second portion" refers to the other leg of the same clamp, which may be helpful in facilitating discussion of movement of one lateral "side"—including both top and bottom portions—with respect to the other lateral "side" of the clip 100.)

There may be a relief recess 124 or other feature provided in one or more of the top and bottom legs 108 and 116, as shown in the Figures. When present, the relief recess 124 may facilitate and accommodate mutual pivoting motion of the structures of those legs near the hinged attachment 114 or 122, and optionally provide a "stop" or rotation-limiting function, as desired.

Figure 3:
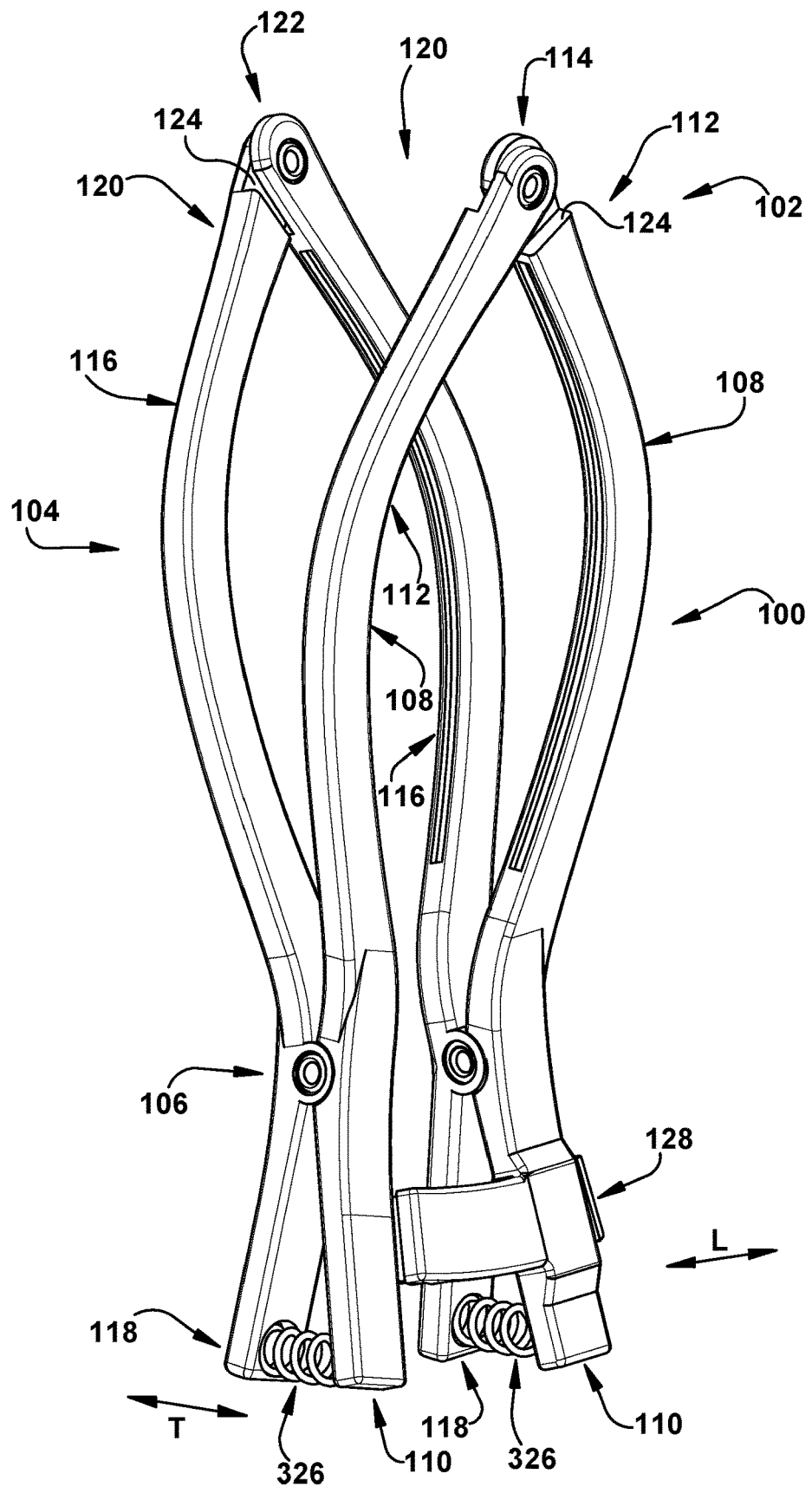
FIG. 3 is a side perspective view of the surgical clip of FIG. 1 in an alternate configuration.

As shown in FIG. 3, the hinged joint 106 may be biased (e.g., via spring(s) 326) to urge at least a portion of the top and bottom clamps 102 and 104 (e.g., the distal top and bottom leg ends 112 and 120) mutually together, in the transverse direction. Though the springs 326 are shown as being coil springs adjacent proximal top and bottom leg ends 110 and 118, any desired type of spring or other biasing member could be used, such as, but not limited to, a leaf spring, a resilient material, or any other desired structure configured to provide a suitable biasing force. Similarly, the biasing mechanism could be located anywhere on the clip 100 as desired. For example, the hinged joint 106 could have an internal spring-bias feature, much like the wire coils of a traditional two-piece wooden clothespin.

At least one selected one of the top and bottom clamps 102 and 104 (e.g., at least one selected pair of the top legs 108 and the bottom legs 116) could include a ratcheting connection 128 to selectively maintain a lateral spacing of the selected pair of legs 108 and 116, in a hemostat-like manner. This ratcheting connection is shown in the bottom view of FIG. 2. Because each top leg 108 is connected to a corresponding bottom leg 116 by the hinged joint 106, it is contemplated that providing a ratcheting connection 128 to only one of the top and bottom clamps 102 and 104 may suffice, in many use environments, to selectively maintain the lateral spacing as desired. When present, the ratcheting connection 128 can be of any suitable type. For example, the ratcheting connection 120 could be engaged by bringing the selected pair of top legs 108 or bottom legs 116 laterally toward one another, and the ratcheting connection 120 would then maintain the thus imposed lateral spacing of the legs until a transverse force is applied to disengage the ratcheting connection 128 and allow the legs to attain different lateral spacing.

As shown schematically in FIG. 1, at least one of the transversely inward facing surfaces of the top and bottom legs 108 and 116 may include a texturized gripping portion 130. When present, this texturized gripping portion 130 could be a knurled surface of the top and/or bottom legs 108 and 116 themselves, or could be a separately provided pad, sleeve, or any other structure suitable to provide gripping and/or cushioning functions, as desired for a particular use environment.

Figure 2:
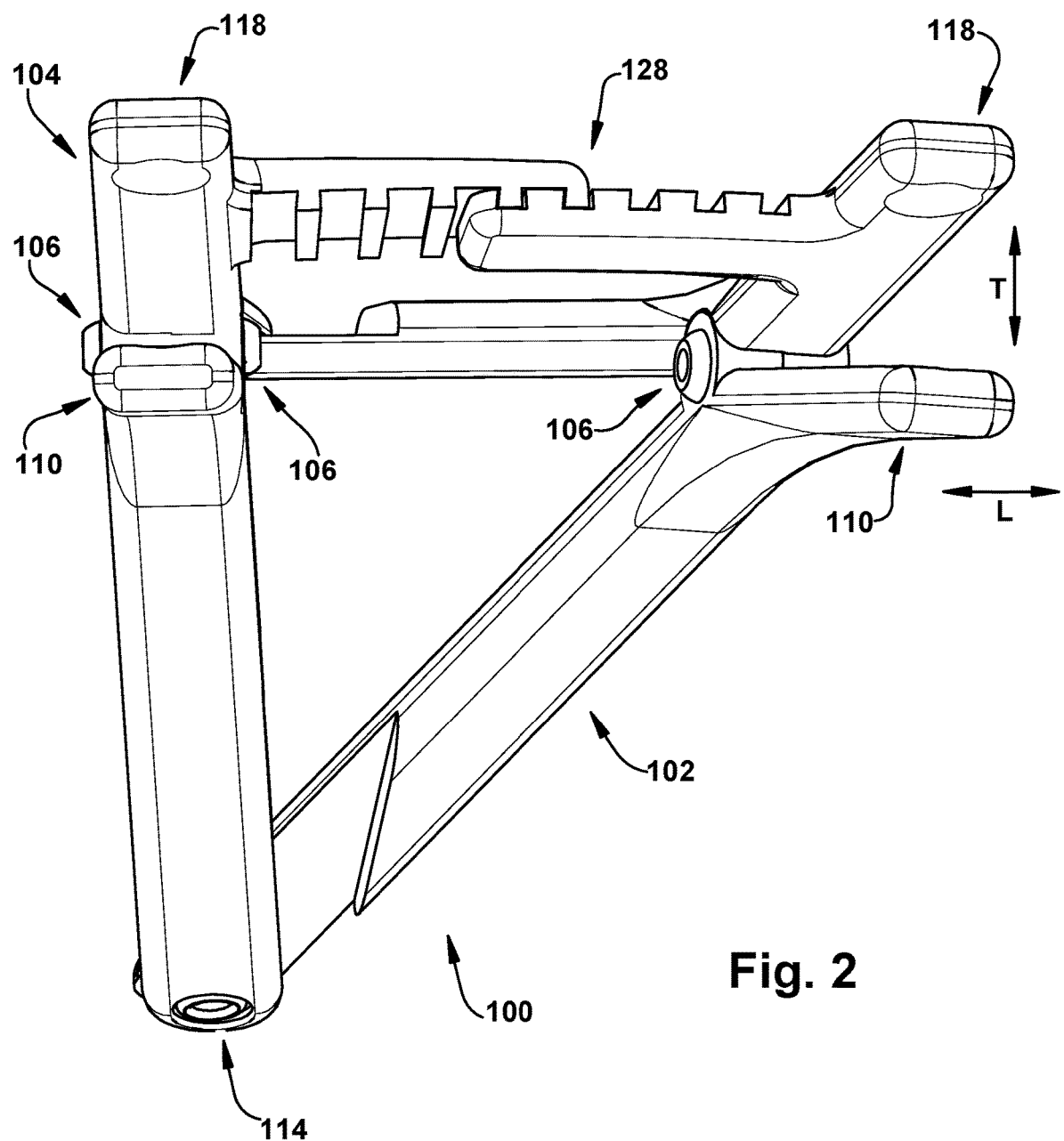
FIG. 2 is a bottom perspective view of the surgical clip of FIG. 1 including an example component.
Figure 5:
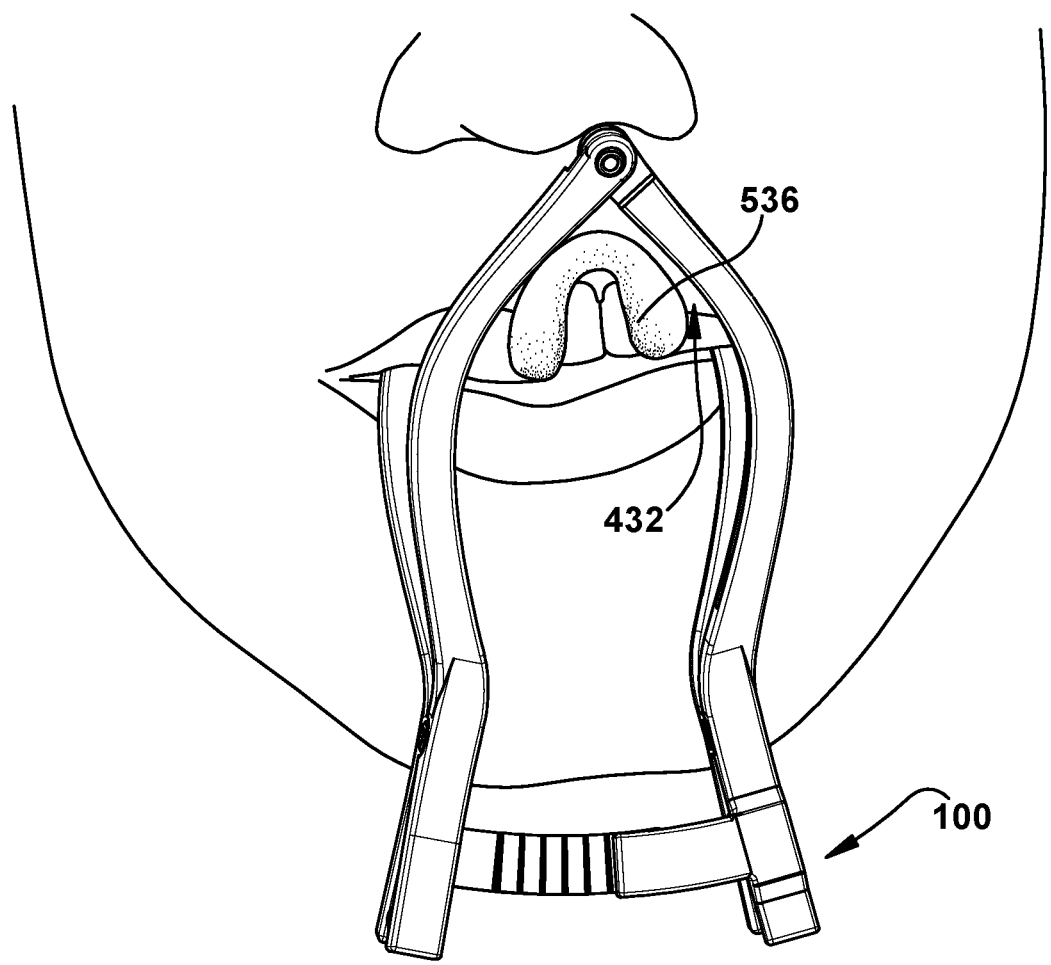
Figure 6:
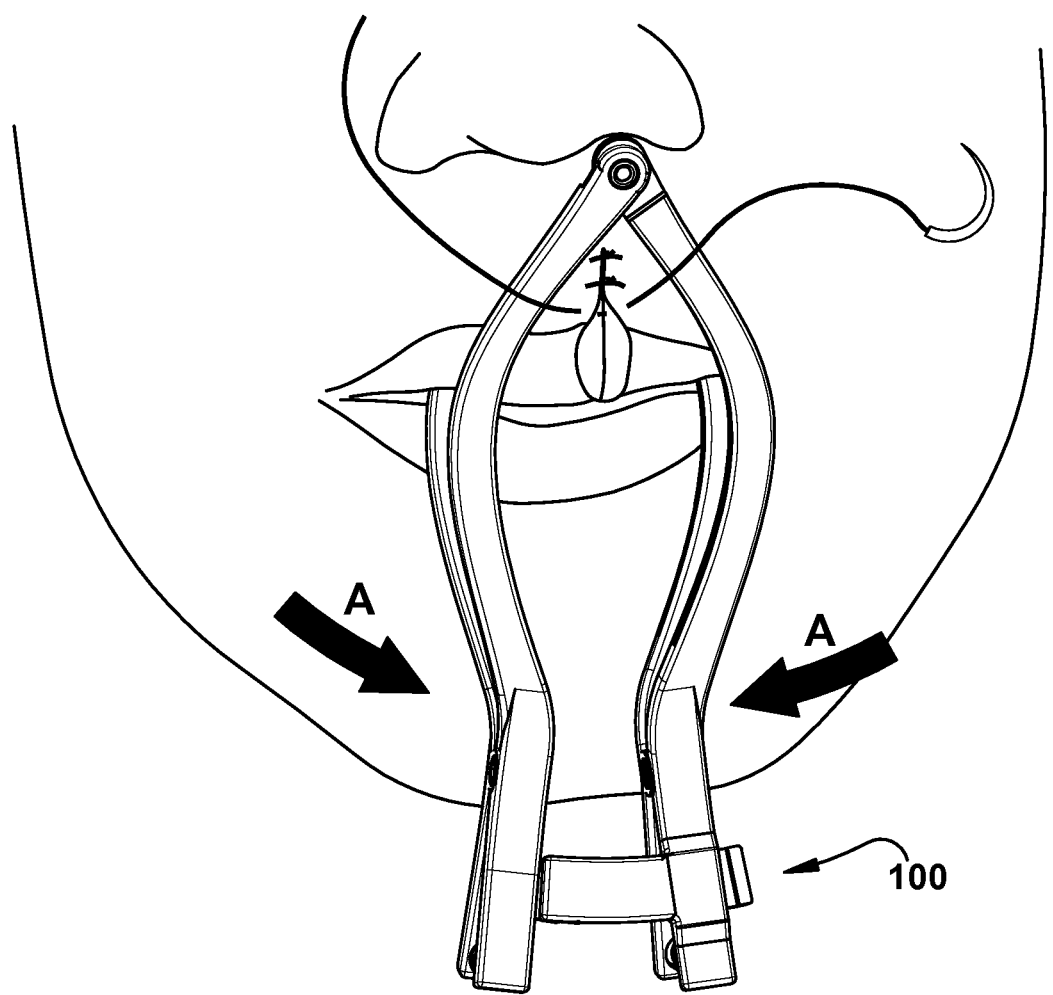

With reference to FIGS. 1-2, the top and bottom clamps 102 and 104 could be substantially linear in the lateral plane. (For clarity, the lateral plane is substantially coincident with the plane of the page in FIGS. 4-6.) For example, when viewed from the transverse direction, the top and bottom clamps 102 and 104 (e.g., all of the top and bottom legs 108 and 116) are substantially linear.

In contrast, as shown in FIGS. 3-6, both of the top and bottom clamps 102 and 104 can include a curved portion in the lateral plane. For example, all of the top and bottom legs 108 and 116 could include a curved portion in the lateral plane, as depicted in FIGS. 3-6. The top and bottom clamps 102 and 104 may include substantially matched curved portions with each other, as shown in FIGS. 3-6. For example, the laterally aligned ones of the top and bottom legs 108 and 116 can include substantially matched curved portions having substantially similar location and degree, but which may be oppositely "facing", as shown. When present, such a curvature may provide a larger area laterally between the legs 108 and 116 within which a surgeon can work, as compared to a clip 100 which is substantially linear in the lateral plane.

It is also contemplated that the curved portions of the top and bottom legs 108 and 116 could be unmatched (not shown) in order to assist the surgeon in grasping and holding the patient's tissue as desired. For example, there may be a bony structure in the way which is to be left unclamped during the procedure. It is also contemplated that at least one of the top and bottom legs 108 and 116 could be at least partially malleable (e.g., made from a material subject to plastic deformation and/or include a "gooseneck" type feature), so that the surgeon can shape the top and bottom clamps 102 and 104 as desired for a particular use environment.

Figure 4:
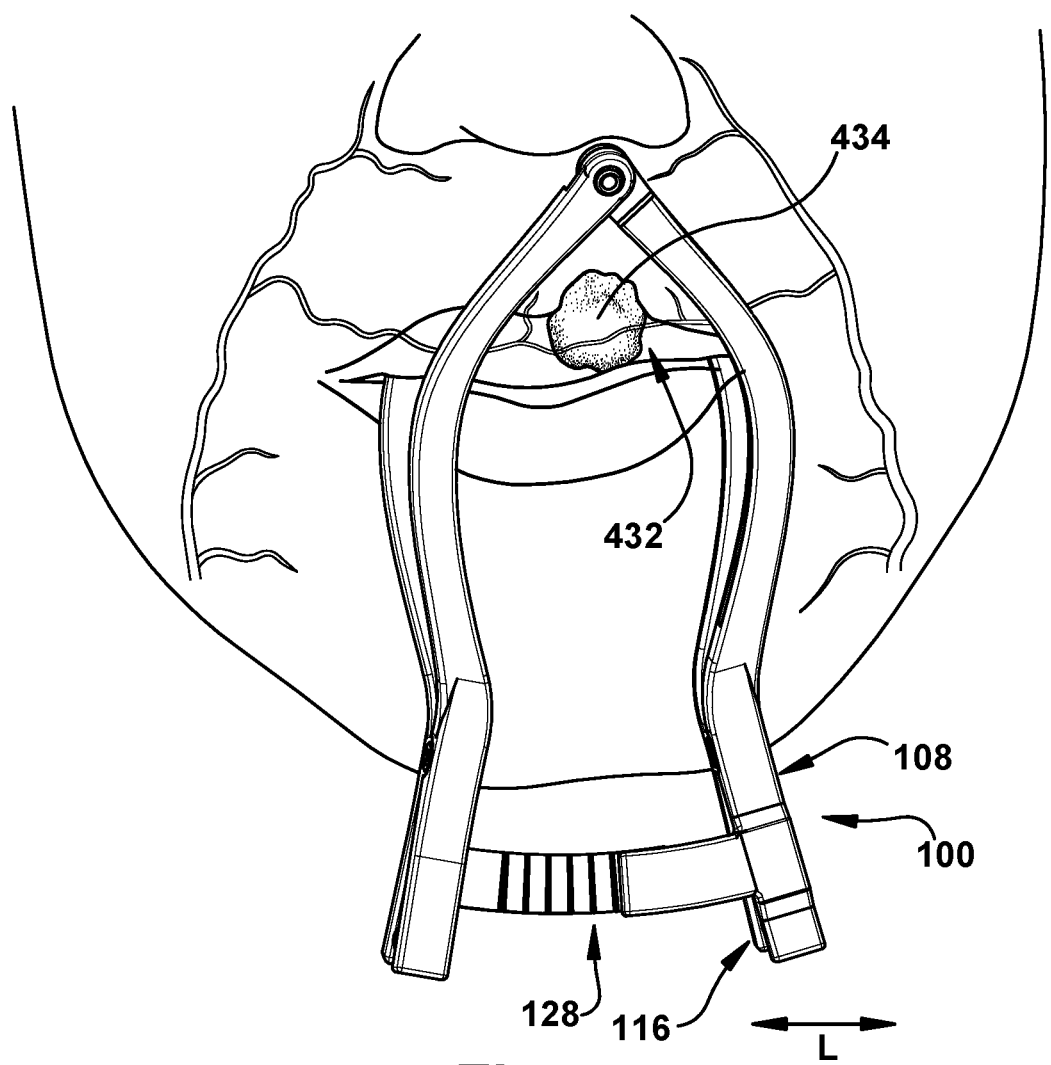
FIGS. 4-6 depict an example sequence of use of the surgical clip of FIG. 1.

With reference now to FIG. 4, the clip 100 is shown as being used to concurrently grasp and move patient tissue in a surgical situation. A clip 100 including any features described herein and/or shown in the Figures, or otherwise configured as desired, is provided.

A transversely directed force is exerted on at least one of the top and bottom clamps 102 and 104 to relatively pivot the top and bottom clamps 102 and 104 about the hinged joint 106 in an opening direction. This exertion of transversely directed force causes distal portions of the top and bottom clamps to separate, in a "clothespin" or "binder clip" type manner. This exertion of transversely directed force may also overcome a transversely directed biasing force (e.g., from spring 326) urging the top and bottom clamps 102 and 104 toward the closing direction. Accordingly, when present, the biasing force could cause the clip 100 to "spring" into a default closed position unless it is being held open by a transversely directed force.

A patient tissue 432 is inserted between the separated distal portions of the top and bottom clamps 102 and 104. For example, in FIGS. 4-6, the patient tissue 432 includes a lesion 434 which is to be excised, and the clip 100 is used to help ligate or cut off blood flow to the area of the lesion.

With the patient tissue 432 inserted therebetween a transversely directed force is exerted on at least one of the top and bottom clamps 102 and 104 to relatively pivot the top and bottom clamps 102 and 104 about the hinged joint 106 in a closing direction. This exertion of transversely directed force causes distal portions of the top and bottom clamps 102 104 to approximate and thereby grasp the patient tissue 432, thus achieving the arrangement shown in FIG. 4.

As a side note, the clips 100 shown in the Figures are designed for a transversely "inward" force (i.e., pressing the top and bottom clamps 102 and 104 toward each other) at the proximal portion of the clip 100—that is, the bottommost portion in FIGS. 1-2—to be used to open the clip 100, and a transversely "outward" force (i.e., opposite the "inward" force) to be used to close the clip 100. However, it is contemplated that, depending upon the configuration of a particular clip 100 the transversely oriented force directions could be reversed for the opening and closing motions.

In any event, once the clip 100 has reached the position with respect to the patient tissue 432 as shown in FIG. 4, the patient tissue 434 is maintained grasped between the top and bottom clamps 102 and 104. This will have the effect of slowing or stopping blood flow to the area laterally "within" the clip, and the surgeon can perform any desired actions upon the patient tissue 434. For example, with reference to FIG. 5, the lesion 434 has been excised, thus leaving a "notch" 536 or void in the patient tissue 434. The surgeon will now want to approximate the lateral edges of this notch 536 so that it can be reattached, such as with sutures, staples, adhesive, or in any other desired manner.

With the patient tissue 432 maintained between the top and bottom clamps 102 and 104, laterally directed force (represented by arrows "A" in FIG. 6) can be exerted concurrently on both the top and bottom clamps 102 and 104 to pivot the first portions of the top and bottom clamps 102 and 104 into a predetermined lateral position with respect to the second portions of the top and bottom clamps 102 and 104. For example, the leftmost ones of the top and bottom legs 108 and 116 can pivot about the hinged attachments 114 and 122 toward the rightmost ones of the top and bottom legs 108 and 116. Thus, the first and second portions of the top and bottom clamps 102 and 104 are pivoted into approximation with each other. As a result, the maintained patient tissue 432 will be compressed laterally between the first and second portions of the top and bottom clamps 102 and 104. The clip 100 thus will hold the patient tissue 432 in a steady and even manner, to allow for any further actions upon the patient tissue 432, such as the suturing shown in FIG. 6. If the clip 100 were not used, the surgeon and/or her assistants would need to manipulate the patient tissue 432 with hemostats or other separate tools, and the approximation would not necessarily happen smoothly or provide a steadily held patient tissue 432 surface upon which the surgeon could work. As a result, the clip 100 can assist with alignment of anatomical features for desired closure or other treatment, and can also reduce or even eliminate the use of epinephrine in the area.

When a ratcheting connection 128 is present between the first and second portions of at least one of the top and bottom clamps 102 and 104, that ratcheting connection 128 could be actuated via the laterally directed force being exerted concurrently on both the top and bottom clamps 102 and 104. The surgeon could then selectively maintain, with the ratcheting connection 128, a desired lateral spacing of the first and second portions of the top and bottom clamps 102 and 104, to assist with attaining the desired working surface upon the patient tissue 432.

When it is no longer desirable for the patient tissue 432 to be held by the clip 100, a transversely oriented force can once again be exerted to urge the clip 100 into the opening position (with the distal top and bottom leg ends 112 and 120 moving apart from one another), in the clip 100 can be moved proximally out of engagement with the patient tissue 432, again much like a clothespin or binder clip would be. The lateral spacing, or pivot condition, of the top and bottom clamps 102 and 104 which was used to approximate the patient tissue 432 is optionally released or reversed before the clip 100 is removed from the patient tissue 432, but does not need to be.

Additionally, it is contemplated that the clip 100 could be immediately applied in a nonsurgical setting by emergency personnel treating a lip laceration, thus acting to slow bloodflow to the region and reduce blood loss. The surgeon later encountering the laceration victim could remove or reposition the clip 100 applied "on the scene", or could even leave it in place to help approximate the wound during surgical treatment.

While aspects of this disclosure have been particularly shown and described with reference to the example aspects above, it will be understood by those of ordinary skill in the art that various additional aspects may be contemplated. For example, the specific methods described above for using the apparatus are merely illustrative; one of ordinary skill in the art could readily determine any number of tools, sequences of steps, or other means/options for placing the above-described apparatus, or components thereof, into positions substantively similar to those shown and described herein. In an effort to maintain clarity in the Figures, certain ones of duplicative components shown have not been specifically numbered, but one of ordinary skill in the art will realize, based upon the components that were numbered, the element numbers which should be associated with the unnumbered components; no differentiation between similar components is intended or implied solely by the presence or absence of an element number in the Figures. Any of the described structures and components could be integrally formed as a single unitary or monolithic piece or made up of separate sub-components, with either of these formations involving any suitable stock or bespoke components and/or any suitable material or combinations of materials; however, the chosen material(s) should be biocompatible for many applications. Any of the described structures and components could be disposable or reusable as desired for a particular use environment. Any component could be provided with a user-perceptible marking to indicate a material, configuration, at least one dimension, or the like pertaining to that component, the user-perceptible marking potentially aiding a user in selecting one component from an array of similar components for a particular use environment. A "predetermined" status may be determined at any time before the structures being manipulated actually reach that status, the "predetermination" being made as late as immediately before the structure achieves the predetermined status. The term "substantially" is used herein to indicate a quality that is largely, but not necessarily wholly, that which is specified—a "substantial" quality admits of the potential for some relatively minor inclusion of a non-quality item. Though certain components described herein are shown as having specific geometric shapes, all structures of this disclosure may have any suitable shapes, sizes, configurations, relative relationships, cross-sectional areas, or any other physical characteristics as desirable for a particular application. Any structures or features described with reference to one aspect or configuration could be provided, singly or in combination with other structures or features, to any other aspect or configuration, as it would be impractical to describe each of the aspects and configurations discussed herein as having all of the options discussed with respect to all of the other aspects and configurations. A device or method incorporating any of these features should be understood to fall under the scope of this disclosure as determined based upon the claims below and any equivalents thereof.

Other aspects, objects, and advantages can be obtained from a study of the drawings, the disclosure, and the appended claims.

I claim:

1. A dual-directional surgical clip, comprising:
    a top clamp; and
    a bottom clamp, hingedly connected to the top clamp at a hinged joint for mutually pivotal transverse motion about the hinged joint;
    wherein the top and bottom clamps each include a hinged attachment at an extreme end thereof, a first portion of each of the top and bottom clamps being in hinged connection with a corresponding second portion of the respective top and bottom clamps for mutually pivotal lateral movement wherein the first and second portions are directly hingedly attached to one another at the hinged attachment.

2. The dual-directional surgical clip of claim 1, wherein both of the top and bottom clamps are substantially linear in a lateral plane.

3. The dual-directional surgical clip of claim 1, wherein both of the top and bottom clamps include a curved portion in a lateral plane.

4. The dual-directional surgical clip of claim 3, wherein the top and bottom clamps include substantially matched curved portions with each other in the lateral plane.

5. The dual-directional surgical clip of claim 1, wherein the hinged joint is biased to urge at least a portion of the top and bottom clamps mutually together.

6. The dual-directional surgical clip of claim 1, wherein a selected one of the top and bottom clamps includes a ratcheting connection to selectively maintain a lateral spacing of the first and second portions of that selected clamp.

7. The dual-directional surgical clip of claim 1, wherein
    the top clamp includes a pair of top legs, each top leg including oppositely disposed proximal and distal top leg ends, the distal top leg ends being connected by the hinged attachment for the mutual pivotal movement along a lateral direction;
    the bottom clamp includes a pair of bottom legs, each bottom leg including oppositely disposed proximal and distal bottom leg ends, the distal bottom leg ends being connected by the hinged attachment for the mutual pivotal movement along the lateral direction; and
    the hinged joint is located proximally from the distal top and bottom leg ends and connects the pairs of top and bottom legs together for the mutual pivotal movement along a transverse direction.

8. A multi-degree-of-freedom surgical clip, comprising:
    a pair of top legs, each top leg including oppositely disposed proximal and distal top leg ends, the distal top leg ends being hingedly attached together for mutual pivotal movement along a lateral direction;
    a pair of bottom legs, each bottom leg including oppositely disposed proximal and distal bottom leg ends, the distal bottom leg ends being hingedly attached together for mutual pivotal movement along the lateral direction; and
    a hinged joint located proximally from the distal top and bottom leg ends and connecting the pairs of top and bottom legs together for mutual pivotal movement along a transverse direction wherein the distal top leg ends are directly hingedly attached to one another, as are the distal bottom leg ends.

9. The multi-degree-of-freedom surgical clip of claim 8, wherein all of the top and bottom legs are substantially linear in a lateral plane.

10. The multi-degree-of-freedom surgical clip of claim 8, wherein all of the top and bottom legs include a curved portion in a lateral plane.

11. The multi-degree-of-freedom surgical clip of claim 10, wherein the laterally aligned ones of the top and bottom legs include substantially similar curved portions to each other in the lateral plane.

12. The multi-degree-of-freedom surgical clip of claim 8, wherein the hinged joint is biased to urge the distal top leg ends and distal bottom leg ends mutually together.

13. The multi-degree-of-freedom surgical clip of claim 8, wherein a selected pair of the top legs and the bottom legs includes a ratcheting connection to selectively maintain a lateral spacing of the selected pair of legs.

14. The multi-degree-of-freedom surgical clip of claim 8, wherein at least one of the transversely inward facing surfaces of the top and bottom legs includes a texturized gripping portion.

15. A method of concurrently grasping and moving patient tissue, the method comprising:
    providing a dual-directional surgical clip including
        a top clamp, and
        a bottom clamp, hingedly connected to the top clamp at a hinged joint for mutually pivotal transverse motion about the hinged joint,
        wherein the top and bottom clamps each include a hinged attachment at an extreme end thereof, a first portion of the top and bottom clamps being in hinged connection with a corresponding second portion of the top and bottom clamps for mutually pivotal lateral movement;
    exerting transversely directed force on at least one of the top and bottom clamps to relatively pivot the top and bottom clamps about the hinged joint in an opening direction, thus causing distal portions of the top and bottom clamps to separate;
    inserting a patient tissue between the separated distal portions of the top and bottom clamps;
    with the patient tissue inserted therebetween, exerting transversely directed force on at least one of the top and bottom clamps to relatively pivot the top and bottom clamps about the hinged joint in a closing direction, thus causing distal portions of the top and bottom clamps to approximate and thereby grasp the patient tissue;
    maintaining the patient tissue grasped between the top and bottom clamps; and
    with the patient tissue maintained between the top and bottom clamps, exerting laterally directed force concurrently on both the top and bottom clamps to pivot the first portions of the top and bottom clamps into a predetermined lateral position with respect to the second portions of the top and bottom clamps.

16. The method of claim 15, wherein exerting laterally directed force concurrently on both the top and bottom clamps includes pivoting the first and second portions of the top and bottom clamps into approximation with each other; and the method includes compressing the maintained patient tissue laterally between the first and second portions of the top and bottom clamps.

17. The method of claim 15, wherein exerting transversely directed force on at least one of the top and bottom clamps to relatively pivot the top and bottom clamps about the hinged joint in an opening direction includes overcoming a transversely directed biasing force urging the top and bottom clamps toward the closing direction.

18. The method of claim 15, wherein exerting laterally directed force concurrently on both the top and bottom clamps includes actuating a ratcheting connection between first and second portions of at least one of the top and bottom clamps; and the method includes selectively maintaining, with the ratcheting connection, a lateral spacing of the first and second portions of the top and bottom clamps.

* * * * *